United States Patent
Masuda et al.

(10) Patent No.: US 6,197,061 B1
(45) Date of Patent: Mar. 6, 2001

(54) IN VITRO PRODUCTION OF TRANSPLANTABLE CARTILAGE TISSUE COHESIVE CARTILAGE PRODUCED THEREBY, AND METHOD FOR THE SURGICAL REPAIR OF CARTILAGE DAMAGE

(76) Inventors: Koichi Masuda, 1214 Longmeadow Dr., Glenview, IL (US) 60025; Eugene J-M. A. Thonar, 14503 S. Pheasant, Lockport, IL (US) 60441; Michael Hejna, 236 Shenstone Rd., Riverside, IL (US) 60546

( * ) Notice: Subject to any disclaimer, the term of this patent is extended or adjusted under 35 U.S.C. 154(b) by 0 days.

(21) Appl. No.: 09/260,741

(22) Filed: Mar. 1, 1999

(51) Int. Cl.[7] .................. A61F 2/02; C12N 5/08; C12N 5/00
(52) U.S. Cl. ............... 623/11.11; 623/915; 435/366; 435/378; 435/401
(58) Field of Search .................... 623/11, 915, 11.11; 435/366, 378, 401

(56) References Cited

U.S. PATENT DOCUMENTS

| | | | |
|---|---|---|---|
| 4,356,261 | 10/1982 | Kuettner | 435/68 |
| 4,673,566 | 6/1987 | Gossen et al. | 424/19 |
| 4,846,835 | 7/1989 | Grande | 623/11 |
| 4,904,259 | 2/1990 | Itay | 623/16 |
| 4,927,761 | 5/1990 | Reading et al. | 435/178 |
| 5,041,138 | 8/1991 | Vacanti et al. | 623/16 |
| 5,053,050 | 10/1991 | Itay | 623/16 |
| 5,067,964 | 11/1991 | Richmond et al. | 623/18 |
| 5,073,491 | 12/1991 | Familletti | 435/240 |
| 5,226,914 | 7/1993 | Caplan et al. | 623/16 |
| 5,286,495 | 2/1994 | Batich et al. | 424/490 |
| 5,294,446 | 3/1994 | Schlameus et al. | 424/489 |
| 5,364,580 | 11/1994 | Prent | 264/138 |
| 5,368,858 | 11/1994 | Hunziker | 424/423 |
| 5,486,359 | 1/1996 | Caplan et al. | 424/93.7 |
| 5,516,532 | 5/1996 | Atala et al. | 424/548 |
| 5,536,656 * | 7/1996 | Kemp et al. | 435/240.23 |
| 5,538,887 | 7/1996 | Peindl et al. | 435/240 |
| 5,549,904 | 8/1996 | Juergensen et al. | 424/423 |
| 5,612,028 | 3/1997 | Sackier et al. | 424/93.7 |
| 5,635,390 | 6/1997 | Peindle et al. | 435/402 |
| 5,648,099 | 7/1997 | Batich et al. | 424/497 |
| 5,667,778 | 9/1997 | Atala | 424/93.7 |
| 5,693,514 | 12/1997 | Dorian et al. | 435/178 |
| 5,693,624 | 12/1997 | Hardy et al. | 514/54 |
| 5,700,289 | 12/1997 | Breitbart et al. | 623/16 |
| 5,700,774 | 12/1997 | Hattersley et al. | 514/2 |
| 5,707,962 | 1/1998 | Chen et al. | 514/12 |
| 5,709,854 | 1/1998 | Griffith-Cima et al. | 424/93.7 |
| 5,713,374 | 2/1998 | Pachence et al. | 128/898 |
| 5,716,404 | 2/1998 | Vacanti et al. | 623/8 |
| 5,716,616 | 2/1998 | Prockop et al. | 424/93.7 |
| 5,723,331 | 3/1998 | Tubo et al. | 435/366 |
| 5,736,396 * | 4/1998 | Bruder et al. | 435/366 |
| 5,786,217 * | 7/1998 | Tubo et al. | 435/402 |
| 5,902,741 * | 5/1999 | Purchio et al. | 435/240.23 |
| 5,908,784 * | 6/1999 | Johnstone et al. | 435/372 |
| 5,932,459 * | 8/1999 | Sittinger et al. | 435/180 |

OTHER PUBLICATIONS

Buckwalter et al., "Structural Differences Between Two Populations of Articular Cartilage Proteoglycan Aggregates," J. of Orthopedic Research 12: 144–148 (1994).

Caplan, "Cell and Molecular Strategies for Massive Bone Repair/Regeneration," Nippon Seikeigeka Gakkai Zasshi 63:692–699 (1989).

Fernandez et al., "The Structure of Anchorin CII, a Collagen Binding Protein Isolated from Chondrocyte Membrane," J. Biol. Chem. 263 (12): 5921–5925 (1988).

(List continued on next page.)

*Primary Examiner*—Jeffrey A. Smith
(74) *Attorney, Agent, or Firm*—Fitch, Even, Tabin & Flannery

(57) ABSTRACT

The present invention is directed to a transplantable cartilage matrix and a method for its in vitro production.

23 Claims, 2 Drawing Sheets

OTHER PUBLICATIONS

Grande et al., "The Repair of Experimentally Produced Defects in Rabbit Articular Cartilage by Autologous Chondrocyte Transplantation," J. Orthopedic Research 7:208–218 (1989).

Hauselmann et al., "Adult Human Chondrocytes Cultured in Alginate Form a Matrix Similar to Native Human Articular Cartilage," Am. J. Physiol. 271:C742–52 (1996).

Hendrickson et al., "Chondrocyte–Fibrin Matrix Transplants for Resurfacing Extensive Articular Cartilage Defect," J. of Orthopedic Research 12:485–497 (1994).

Johnson et al., "The Early Response of Articular Cartilage to ACL Transection in a Canine Model," Exp. Pathol. 38:37–52 (1990).

Kempson, "Age–related Changes in the Tensile Properties of Human Articular Cartilage: A Comparative Study Between the Femoral Head of the Hip Joint and the Talus of the Ankle Joint," Biochem. Biophys. Acta. 1075:223–230 (1991).

Knudson, "Hyaluronan Receptor–Directed Assembly of Chondrocyte Pericellular Matrix," J. Biol. Chem. 267:23007–23014 (1992).

Kwan et al., "The Effect of Storage on the Biomechanical Behavior of Articular Cartilage—A Large Strain Study," J. Biomech, Eng. 114:149–153 (1992).

MacGinitie et al., "Electric Field Stimulation Can Increase Protein Synthesis in Articular Cartilage Explants," J. of Orthopedic Research 12:151–160 (1994).

Mizrahi et al., "The Instantaneous Deformation of Cartilage: Efects of Collagen Fiber Orientation and Osmotic Stress," Biorheology 23:311–330 (1986).

Schinagl et al., "Depth–Dependent Confined Compression Modulus of Full–Thickness Bovine Articular Cartilage," J. of Orthopedic Research 15:499–506 (1997).

Wu et al., "Identification of Cross–linking Sites in Bovine Cartilage Type IX Collagen Reveals an Antiparallel Type II–Type IX Molecular Relationship and Type IX to Type IX Bonding," J. Biol. Chem. 267 (32): 23007–23014 (1992).

Chiba et al., "Metabolism of the Extracellular Matrix Formed by Intervertebral Disc Cells Cultured in Alginate," Spine, vol. 22, No. 24, Dec. 15, 1997, pp. 2885–2893.

Hauselman et al., "Adult Human Chondrocytes Cultured in Alginate Form a Matrix Similar to Native Human Articular Cartilage," Am. J. Physiol. 271 (Cell Physiol. 40): C742–C752, 1996.

Huch et al., "Effects of Recombinant Human Osteogenic Protein 1 on the Production of Proteoglycan Prostaglandin $E_2$, and Interleukin–1 Receptor Antagonist by Human Articular Chondrocytes Cultured in the Presence of Interleukin–1β," Arthritis & Rheumatism, vol. 40, No. 12, Dec., 1997, pp. 2157–2161.

Masuda et al., "Age–Related Differences in the Metabolism of Hyaluronan Present in Two Distinct Compartments of the Matrix Formed by Articular Chondrocytes In Vitro," $41^{st}$ Annual Meeting, Orthopaedic Research Society, Feb. 13–16, 1995, Orlando, Florida.

Mok et al., "Aggrecan Synthesized by Mature Bovine Chondrocytes Suspended in Alginate," J. of Biol. Chem., vol. 269, No. 52, Dec. 30, 1994, pp. 33021–33027.

Petit et al., "Characterization of Crosslinked Collagens Synthesized by Mature Articular Chondrocytes Cultured in Alginate Beads: Comparison of Two Distinct Matrix Compartments'" Experimental Cell Research 225, 1996, 151–161.

Shakibaei et al., "Differentiation of Mesenchymal Limb Bud Cells to Chondrocytes in Alginate Beads," Cell Biology International, vol. 21, No. 2, pp. 75–86 (1997).

* cited by examiner

IN VITRO PRODUCTION OF TRANSPLANTABLE CARTILAGE TISSUE COHESIVE CARTILAGE PRODUCED THEREBY, AND METHOD FOR THE SURGICAL REPAIR OF CARTILAGE DAMAGE

The present invention relates to the method of production of cartilage tissue for surgical implantation into human joints for the purpose of filling defects of the articular cartilage or replacing damaged or degenerated cartilage.

BACKGROUND OF THE INVENTION

Cartilage Injury and Repair:

Human joint surfaces are covered by articular cartilage, a low friction, durable material that distributes mechanical forces and protects the underlying bone. Injuries to articular cartilage are common, especially in the knee. Data from the Center for Disease Control (CDC) and clinical studies have suggested that approximately 100,000 articular cartilage injuries occur per year in the United States. Such injuries occur most commonly in young active people and result in pain, swelling, and loss of joint motion. Damaged articular cartilage does not heal. Typically, degeneration of the surrounding uninjured cartilage occurs over time resulting in chronic pain and disability. Cartilage injuries therefore frequently lead to significant loss of productive work years and have enormous impact on patients' recreation and lifestyle.

Joint surface injuries may be limited to the cartilage layer or:may extend into the subchondral bone. The natural histories of these types of injuries differ. Cartilage injuries which do not penetrate the subchondral bone have limited capacity for healing (1). This is due to properties inherent to the tissue. Nearly 95 per cent of articular cartilage is extracellular matrix (ECM) that is produced and maintained by the chondrocytes dispersed throughout it. The ECM provides the mechanical integrity of the tissue. The limited number of chondrocytes in the surrounding tissue are unable to replace ECM lost to trauma. A brief overproduction of matrix components by local chondrocytes has been observed (2); however, the response is inadequate for the repair of clinically relevant defects. Cellular migration from the vascular system does not occur with pure chondral injury and extrinsic repair is clinically insignificant.

Osteochondral injuries, in which the subchondral bone plate is penetrated, can undergo healing due to the influx of reparative cells from the bone marrow (1). Numerous studies have shown, however, that the complex molecular arrangement of the ECM necessary for normal cartilage function is not recapitulated. The repair response is characterized by formation of fibrocartilage, a mixture of hyaline cartilage and fibrous tissue. Fibrocartilage lacks the durability of articular cartilage and eventually undergoes degradation during normal joint use Many osteochondral injuries become clinically asymptomatic for a period of a few to several years before secondary degeneration occurs. However, like isolated chondral injuries, these injuries ultimately result in poor joint function, pain, and disability.

Molecular Organization of the ECM:

The physical properties of articular cartilage are tightly tied to the molecular structures of type II collagen and aggrecan. Other molecules such as hyaluronan and type IX collagen play important roles in matrix organization. Type,II collagen forms a 3-dimensional network or mesh that provides the tissue with high tensile and shear strength (3). Aggrecan is a large, hydrophilic molecule, which is able to aggregate into complexes of up to 200 to $300\times10^6$ Daltons (4)]. Aggrecan molecules contain glycosaminoglycan chains that contain large numbers of sulfate and carboxylate groups. At physiological pH, the glycosaminoglycan chains are thus highly negatively charged (5). In cartilage, aggrecan complexes are entrapped within the collagen network. A Donnan equilibrium is established in which small cations are retained by electrical forces created by the sulfate and carboxylate groups (6). Water is in turn retained by the osmotic force produced by large numbers of small cations in the tissue.

When the joint is mechanically loaded, movement of water results in perturbation of the electrochemical equilibrium. When the load is removed, the Donnan equilibrium is reestablished and the tissue returns to its pre-loaded state (7). The physical properties of articular cartilage are tightly tied to the molecular structures of type II collagen and aggrecan. Other matrix molecules, such as hyaluronan (8) and type IX collagen (9), play important roles in matrix organization. Failure to restore the normal molecular arrangement of the ECM leads to failure of the repair tissue over time, as demonstrated by the poor long-term performance of fibrocartilage as a repair tissue (10).

Distinct compartments have been demonstrated within the ECM. These differ with respect to the composition and turnover of matrix macromolecules. Immediately surrounding each chondrocyte is a thin shell of ECM characterized by a relatively rapid turnover of matrix components (11). This region is termed the pericellular matrix (11). Surrounding the pericellular matrix is the territorial matrix. Further from the cells is the interterritorial matrix (11). Turnover of matrix macromolecules is slower in the interterritorial matrix than in the pericellular and territorial matrices (11). The role that these various compartments play in the function of the tissue as a whole is unclear. From the perspective of articular cartilage repair, however, they represent a higher level of matrix organization that must be considered in the restoration of injured tissue.

Surgical Treatment of Articular Cartilage Injury:

Current methods of surgical restoration of articular cartilage fall into three categories: (1) stimulation of fibrocartilaginous repair; (2) osteochondral grafting; and (3) autologous chondrocyte implantation. Fibrocartilage, despite its relatively poor mechanical properties, can provide temporary symptomatic relief in articular injuries. Several surgical techniques have been developed to promote the formation of fibrocartilage in areas of cartilage damage. These include subchondral drilling, abrasion, and microfracture. The concept of these procedures is that penetration of the subchondral bone allows chondroprogenitor cells from the marrow to migrate into the defect and effect repair. The clinical success rate of this type of treatment is difficult to assess. In published series, success rates as high as 70% are reported at 2 years; however, the results deteriorate with time. At five years post-treatment, the majority of patients are symptomatic.

In osteochondral grafting, articular cartilage is harvested with a layer of subchondral bone and implanted into the articular defect. Fixation of the graft to the host is accomplished through healing of the graft bone to the host bone. The major advantage of this technique is that the transplanted cartilage has the mechanical properties of normal articular cartilage and therefore can withstand cyclical loading. The major disadvantages are donor-site morbidity (in the case of autograft) and risk of disease transmission (in the case of allograft). Additionally, tissue rejection can occur with allografts which compromises the surgical result. Osteochondral autografting (mosaicplasty) has demonstrated short-term clinical success . The long-term effectiveness is unknown. Osteochondral allografts are successful in approximately 65% of cases when assessed at 10 years post-implantation, but are generally reserved for larger areas of damage extending deep into the subchondral bone.

Autologous chondrocyte implantation is a method of cartilage repair that uses isolated chondrocytes. Clinically, this is a two-step treatment in which a cartilage biopsy is first obtained and then, after a period of ex vivo processing, cultured chondrocytes are introduced into the defect (12). During the ex vivo processing, the ECM is removed and the chondrocytes are cultured under conditions that promote cell division. Once a suitable number of cells are produced, they are implanted into the articular defect. Containment is provided by a patch of periosteum which is sutured to the surrounding host cartilage. The cells attach to the defect walls and produce the extracellular matrix in situ. The major advantages of this method are the use of autologous tissue and the ability to expand the cell population. Difficulties with restoration of articular cartilage by this technique fall into three categories: cell adherence, phenotypic transformation, and ECM production.

Cell adherence. The success of implantation of individual cells (without ECM) is critically dependent upon the cells attaching to the defect bed. Cartilage ECM has been shown to have anti-adhesive properties, which are believed to be conferred by small proteoglycans, dermatan sulfate, and heparan sulfate. Normal chondrocytes possess cell-surface receptors for type II collagen (13) and hyaluronan (11), but it is not clear to what extent ex-vivo manipulated cells possess receptors for these matrix molecules that are functional. An in vitro study of chondrocyte binding to ECMs suggests that the interaction is weak. An in vivo study in rabbits suggests that only 8% of implanted chondrocytes remain in the defect bed after implantation.

Phenotypic transformation. During the process of expanding the cell population in vitro, chondrocytes usually undergo phenotypic transformation or dedifferentiation (14). Morphologically, the cells resemble fibroblasts. Synthesis of type II collagen and aggrecan is diminished and synthesis of type I collagen, typical of fibrocartilage, is increased. Limited data exist to support the contention that the cells redifferentiate in situ following implantation. Reestablishment of the chondrocytic phenotype is critical to the success of the repair process, as tissue produced by cells which are phenotypically fibroblastic functions poorly as a replacement for articular cartilage.

ECM production. Prior to implantation, the cultured chondrocytes are enzymatically denuded of ECM. The cells are injected into the defect bed as a suspension. The graft construct is incapable of bearing load and must be protected from weight bearing for several weeks to months. Limited data exist on the quality of the ECM that is ultimately produced. It has been characterized as hyaline-like tissue at second-look arthroscopy two years post-implantation [Petersen, L., personal communication]. The overall recovery period from this form of treatment is 9–12 months. Good or excellent clinical results are achieved in approximately 85% of femoral condyle lesions 2 years post-implantation. However, it is not clear whether the clinical results will be maintained over longer follow-up periods.

Tissue Engineering:

Each of the current methods of cartilage repair has substantial limitations. As a result, several laboratory approaches to production of cartilage tissue in vitro have been proposed. These generally involve seeding of cultured cells (either chondrocytes or pluripotential stem cells) into a biological or synthetic scaffold. The major drawbacks of this type of approach are: (1) difficulty in attaining or maintaining the chondrocyte phenotype; (2) unknown biological effects of the scaffold material on the implanted and native chondrocytes and other joint tissues; and (3) limited attachment of the engineered tissue construct to the defect bed.

The present invention involves the production of an implantable cartilage tissue. Its method of preparation and composition address the major problems encountered with current techniques of cartilage repair. The major advantages, features and characteristics of the present invention will become more apparent upon consideration of the following description and the appended claims.

SUMMARY OF THE INVENTION

The present invention relates to a transplantable cartilage matrix and a method for its production. Cartilage tissue produced by this method has properties that, with time in culture, become similar to those of a naturally occurring cell-associated ECM. At the time of reimplantation, the matrix in the cartilage tissue has a high rate of turnover (i.e. it is metabolically active). It is rich in cartilage-specific aggrecan proteoglycans and contains enough long hyaluronan chains to allow all these aggrecan molecules to form large aggregates of very large size, but it is relatively poor in collagen pyridinium crosslinks. These properties enhance the implantability of the tissue and subsequent maturation of the tissue in situ following implantation, which leads to integration with the host.

In accordance with the method of the invention, chondrocytes are isolated from tissues containing chondrogenic cells. The isolated chondrogenic cells are cultured in alginate culture for an amount of time effective for allowing formation of a chondrogenic cell-associated matrix. In an important aspect of the invention, the cell-associated matrix has at least about 5 mg/cc$^3$ of aggrecan, a ratio of aggrecan to hyaluronan (mg/mg) between about 10:1 and about 200:1, and a ratio of aggrecan to collagen (mg/mg) between about 1:1 to about 10:1.

Chondrogenic cells, each with a pericellular matrix, are recovered and cultured on a semipermeable membrane system in the presence of serum or serum containing exogenously added growth factor(s). The chondrogenic cells with cell-associated matrix are cultured for a time effective for formation of a cohesive cartilage matrix.

In an important aspect, the invention relates to the use of such in vitro-produced articular tissue in the surgical repair of cartilage damage. Such damage would include acute partial and full thickness chondral injuries, osteochondral injuries, and degenerative processes. Surgical treatment includes open surgical techniques (arthrotomy) and arthroscopic application/insertion of the in vitro-produced cartilaginous tissue.

DETAILED DESCRIPTION

Figure 1:
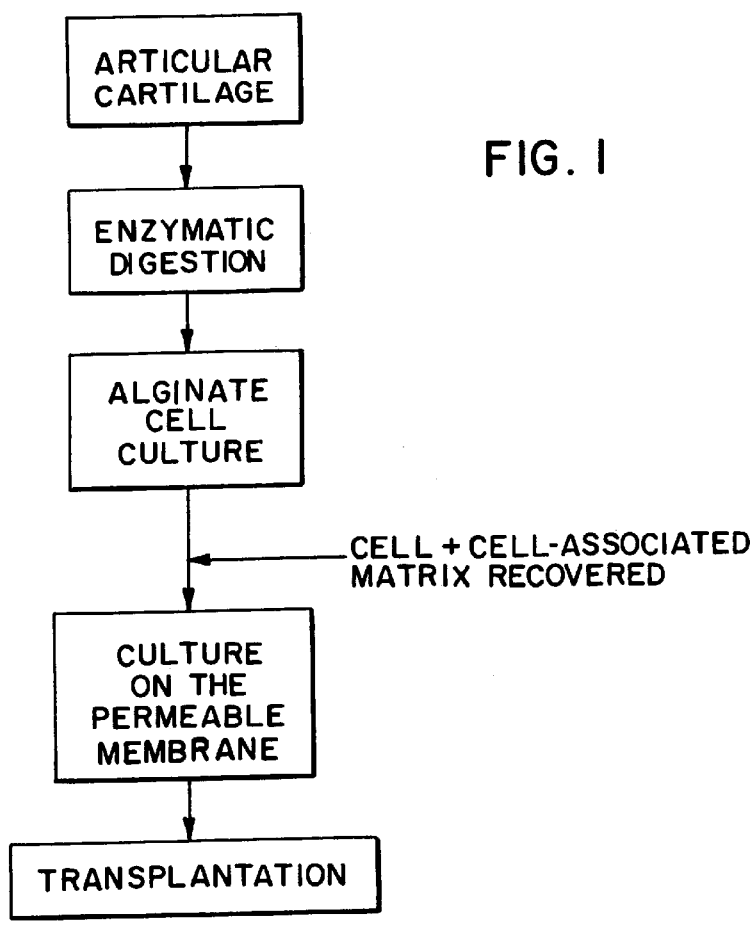
FIG. 1 generally illustrates the overall process for the production of transplantable cartilage matrix in accordance with the present invention.

A generalized process of the present invention is set forth in FIG. 1. In accordance with the invention, chondrocytes are isolated and cultured in alginate. The resulting chondrocytes, each with a cell-associated matrix, are recovered and then further cultured on a semipermeable membrane. The resulting cartilage tissue then is utilized for transplantation.

Isolation of Chondrocytes/Chondrogenic Cells

Chondrogenic cells useful in the practice of the invention may be isolated from essentially any tissue containing chondrogenic cells. As used herein, the term "chondrogenic cell" is understood to mean any cell which, when exposed to appropriate stimuli, may differentiate into a cell capable of producing and secreting components characteristic of cartilage tissue. The chondrogenic cells may be isolated directly from pre-existing cartilage tissue, for example, hyaline cartilage, elastic cartilage, or fibrocartilage. Specifically, chondrogenic cells may be isolated from articular cartilage (from either weight-bearing or non-weight-bearing joints), costal cartilage, nasal cartilage, auricular cartilage, tracheal cartilage, epiglottic cartilage, thyroid cartilage, arytenoid cartilage and cricoid cartilage.

Alternatively, chondrogenic cells may be isolated from bone marrow. See for example, U.S. Pat. Nos. 5,197,985 and 4,642,120, and Wakitani et al. (1994) J. bone Joint Surg. 76:579-591, the disclosures of which are incorporated by reference herein.

Culture in Alginate for the Production of Chondrocyte Cell-associated Matrix

In accordance with the present invention, chondrocytes/ chondrogenic cells isolated from the tissue are resuspended at a density of at least about 104 cells/ml in a solution of sodium alginate. The cells cultured under conditions effective for maintaining their spherical conformation conducive to the production, upon the chondrocyte membrane, of a cell-associated matrix similar to that found in vivo. In an important aspect, chondrocytes are cultured in alginate for at least about five days to allow for formation of the cell-associated matrix. Culture media used may contain a stimulatory agent, such as fetal bovine serum, to enhance the production of the cell-associated matrix.

In an alternative aspect of the invention, the culture medium for the chondrocytes may further include exogenously added specific growth factors. The addition of specific growth factors, for example those not already present'in fetal bovine serum, such as osteogenic protein-1, may act as an effective stimulator of matrix formation. Growth factors (other than those present in fetal bovine serum) may be advantageous as they are becoming available as human recombinant proteins. The use of human growth factors is advantageous in as far as they are less likely to cause an immune response in thejoint (the use of fetal bovine serum requires extensive rinsing of the newly-formed tissue prior to its implantation). In this aspect of the invention, growth factor is added to the medium in an amount to near-maximally stimulate formation of the cell-associated matrix.

In an other important aspect of the invention, amplification of chondrocytes or chondrogenic cells in alginate does not induce loss of the chondrocyte phenotype as occurs when amplification is performed in monolayer culture. As used herein, "chondrocyte phenotype" refers to a cell that has (i)a spherical shape and the ability to synthesize and accumulate within the matrix significant amounts of (ii) aggrecan and (iii) type II collagen without (iv) accumulating within the matrix an effective amount of type I collagen. As used herein, a minimal amount of collagen type I means less than about 10% of all collagen molecules that become incorporated within the matrix. Chondrocytes cultured in alginate retain their spherical shape (typical of chondrocytes) and maintain a large amount of matrix. The matrix resembles hyaline cartilage histologically and is rich in aggrecan and collagen type II.

In addition to the three parameters already mentioned, a phenotypically stable chondrocyte must retain the ability to effectively incorporate the major macromolecules into a cartilage-like matrix. Normal chondrocytes may express small amounts of mRNA for collagen type I that they do not translate. Further, articular chondrocytes cultured in alginate beads for several months may synthesize some collagen type I molecules, but the latter never become incorporated into the forming matrix. Consequently, the appearance of small amounts of newly-synthesized collagen type I molecules in the medium does not necessarily denote the onset of dedifferentiation. Further, hyaluronan is not a marker of the chondrocytic phenotype since it is synthesized in large amounts by many other cell types. However, it is an essential constituent of the cartilage matrix.

Cells that are phenotypically stable should synthesize at least about 10 times more aggrecan than collagen (on a mass basis). Further, the ratio of aggrecan to hyaluronan in the matrix should always remain above about 10.

Chondrocyte with Cell-associated Matrix

Culture of chondrocytes in alginate results in the production of an ECM which is organized into two compartments: a cell-associated matrix compartment which metabolically resembles the pericellular and territorial matrices of native tissues, and (ii) a further removed matrix compartment which metabolically resembles the interterritorial matrix of native tissue.

The formation of a highly structured cell-associated matrix around each chondrocyte is important for several reasons. First, the cell-associated matrix is anchored to the cell via receptors such as anchorin CII (which binds to collagen)and CD44 (which binds to hyaluronan in proteoglycan aggregates). Once this matrix has been reestablished, the cells are much less likely to become dedifferentiated. Second, the chondrocyte turns over proteoglycan aggrecan and thus remodels this matrix relatively rapidly. The chondrocyte is much less effective in remodeling the further removed matrix.

In an important aspect of the invention, the cell-associated matrix compartment of the ECM produced during culture in alginate includes aggrecan (the major cartilage proteoglycan), collagen types II, IX and XI, and hyaluronan. Aggrecan molecules are formed principally in aggregates bound to receptors (including CD44) on the chondrocyte cell membrane via hyaluronan molecules.

The relative proportions of each component in the cell-associated matrix vary depending on the length of time in culture. In an important aspect of the invention, the cell-associated matrix has at least about 5 mg/cc$^3$ of aggrecan, a ratio of aggrecan to hyaluronan (mg/mg) between 10:1 and 200:1, and a ratio of aggrecan to collagen (mg/mg) from 1:1 to about 10:1. Further, the molecular composition of the cell-associated matrix (around each cell) and further removed matrix (between the cells) can be altered by specific modifications of the culture conditions. These modifications involve the physical arrangement of the culture system and application of various growth factors. Manipulation of matrix production and organization are central to the engineering of articular cartilage in vitro for surgical treatment of cartilage injury.

In an important aspect of the invention, the contents of collagen and of the pyridinoline crosslinks of collagen increase with time of culture. The crosslinks in particular show a dramatic increase in concentration after two weeks of culture. By keeping the length of the culture period relatively short, the collagen fibrils in the cell-associated matrix do not become overly crosslinked. A tissue that has good functional properties but is relatively deficient in crosslinks is easier to mold and more likely to become integrated within the host cartilage than a harder, crosslink-rich tissue.

Recovery of Chondrocytes with their Cell-associated Matrix

Figure 2:
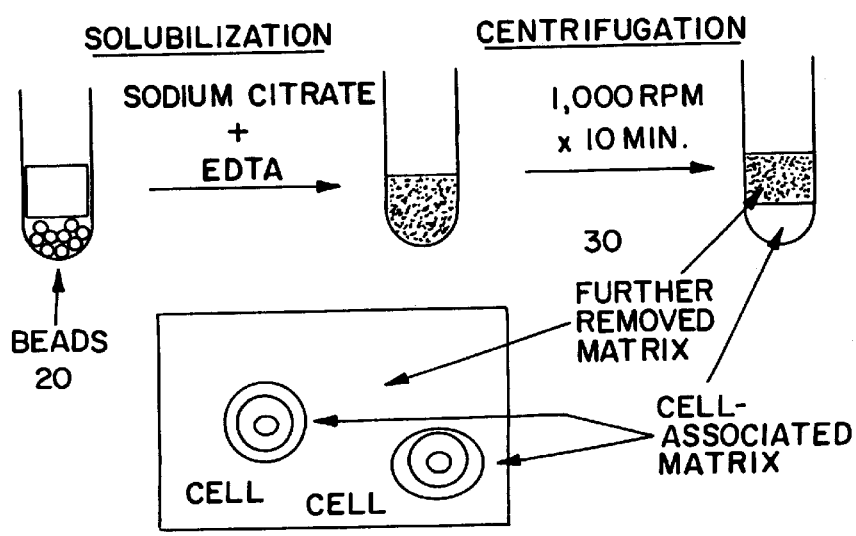
FIG. 2 describes a method for the separation of cells and their cell-associated matrix from the further removed matrix and alginate gel.

Recovery of chondrocytes with their cell-associated matrix is accomplished by solubilizing alginate beads after a sufficient culture period. One approach is set forth in FIG. 2. Alginate beads 20 are first solubilized using known techniques. The resulting cell suspension then is centrifuged, separating the cells with their cell-associated matrix 40 (in the pellet) from the components of the further removed matrix 30 (in the supernatant).

Culturing the Chondrocyte with their Cell-associated Matrix on a Semipermeable Membrane.

Figure 3:
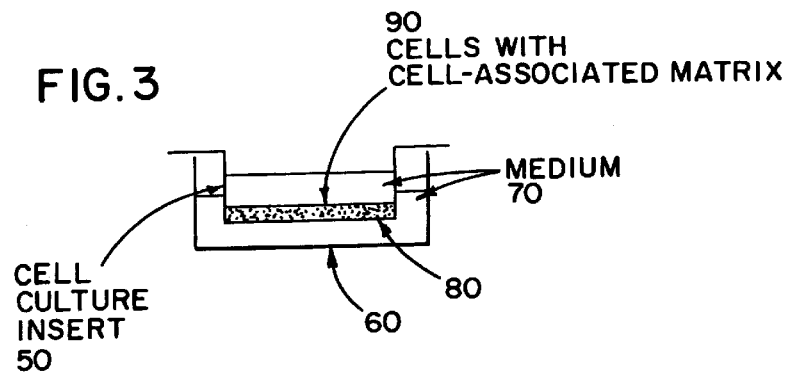
FIG. 3 shows a culture method on a semipermeable membrane.

In this aspect of the invention, the chondrocytes with their cell-associated matrix isolated as described above, are further cultured on a semipermeable membrane. The semipermeable culture system of the invention is shown in FIG. 3.

In accordance with the present invention, a cell culture insert 50 is placed into a plastic support frame 60. Culture medium 70 flows around the cell culture insert 50. In an important aspect of the invention, cell culture insert 50 includes a semipermeable membrane 80.

The semipermeable membrane 80 allows medium to flow into the cell culture insert in an amount effective for completely immersing the chondrocytes and their cell-associated matrix 90.

In an important aspect of the invention, the semipermeable membrane 80 allows the chondrocytes to have continuous access to nutrients while allowing the diffusion of waste products from the vicinity of the cells. In this aspect, the membrane should have a pore size effective to prevent migration of chondrocytes through the pores and subsequent anchoring to the membrane. In this aspect of the invention, the pore size should not be more than about 5 microns. Further, the membrane utilized should have a pore density effective for providing the membrane with sufficient strength so that it can be removed from its culture frame without curling, and with sufficient strength such that the tissue on the membrane can be manipulated and cut to its desired size. In this aspect of the invention, the membrane has a pore density of at least about $8\times10^5$ pores/cm$^2$. The membrane may be made of any material suitable for use in culture. Examples of suitable membrane systems include but are not restricted to: (i) Falcon Cell Culture Insert [Polyethylene terephthalate (PET) membrane, pore size 0.4 or 3.0 microns, diameter 12 or 25 mm]; (ii) Coaster Transwell Plate [Polycarbonate membranes, pore size, 0.1, 0.4, 3.0 or 5.0 microns, diameter 12 or 24.5 mm]; (iii) Nunc Tissue Culture Insert (Polycarbonate Membrane Insert: pore size, 0.4 or 3.0 microns, diameter 10 mm or 25 mm); Millicell Culture Plate Insert (PTFE (polytetrafluoroethylene) membrane, polycarbonate, pore size 0.4 or 3.0 microns, diameter 27 mm]).

The beads containing chondrocytic cells are first cultured in equal parts of Dulbecco's modified Eagle medium and Ham's F12 medium containing 20% fetal bovine serum (Hyclone, Logan, UT), about 25µg/ml ascorbate and 50µg/ml gentamicin or another antibiotic(Gibco). In an alternative approach, the beads are cultured in another type of medium conducive to the maintenance of chondrocytes in culture. In an alternative approach, the beads are cultured in a closed chamber that allows for continuous pumping of medium. In an important aspect, the medium contains fetal bovine serum containing endogenous insulin-like growth factor-1 at a concentration of at least about 10 ng/ml. In this usage, fetal bovine serum may also be considered a growth factor. Suitable growth factors that may be exogenously added to the medium to maximally stimulate formation of the cell-associated matrix include but are not limited to osteogenic protein-1 (OP-1), bone morphogenic protein-2 and other bone morphogenetic proteins, transforming growth factor beta, and insulin-like growth factor.

In another aspect of the invention, cells with their reestablished cell-associated matrix are further cultured in medium on the semipermeable membrane for an amount of time effective for allowing formation of a cohesive cartilage matrix. Culture times will generally be at least about 3 days under standard culture conditions. Partial inhibition of matrix maturation prior to implantation is important in providing a matrix that is not as stiff as mature cartilage, but which has enough tensile strength to retain its shape and structure during handling. Such a tissue should be malleable enough to be press fitted into the defect.

In an important aspect of the invention, mechanical properties of the cartilage matrix can be controled by increasing or decreasing the amount of time that the cartilage tissue is cultured on the membrane. Longer culture time will result in increased crosslink densities.

Cartilage Matrix

In an important aspect of the invention, the cartilage matrix that forms on the semipermeable membrane has a concentration of aggrecan of at least about 5 mg/cc$^3$. The cartilage matrix contains an amount of hyaluronan effective for allowing all the newly synthesized molecules to become incorporated into proteoglycan aggregates. The matrix of the tissue formed on the membrane contains aggregated aggrecan molecule at a concentration not less than 5 mg/cc$^3$, a ratio of aggrecan to hyaluronan of about 10:1 to about 200:1, and a ratio of aggrecan to collagen of about 1:1 to about 10:1. In addition, the short period of culture ensures that concentration of pyridinium crosslinks remains low enough to permit remodeling of the tissue in vivo but high enough to allow the orthopedic surgeon to handle it easily.

In an important aspect, cartilage matrix which forms on the membrane should have a thickness of less than about 2 mm, as cells in a thicker sheet are not likely to gain access to nutrients as readily. Cartilage matrix will generally have a disk-like structure conforming to the membrane; however, there is no requirement that the cartilage matrix have a disk-like structure. In this aspect of the invention, the shape of the cartilage matrix should be effective for allowing an orthopedic surgeon to handle the tissue (either a disk or sheet) and cut it into the size needed for a press fit into a defect. The size of the cartilage matrix will generally be slightly bigger than the size of the defect.

The following examples illustrate methods for carrying out the invention and should be understood to be illustrative of, but not limiting upon, the scope of the invention which is defined in the appended claims.

EXAMPLES

Example I

METHODS

Chondrocytes

Feasibility studies were performed using chondrocytes from young bovine articular cartilage as described below. A similar approach can be (and has been) used to promote cartilage matrix formation by human adult articular chondrocytes.

Culture Conditions

Full-thickness articular cartilage is dissected from the metacarpophalangeal joints of 14- to 18-month-old bovine steers—special attention is given to prevent contamination by synovial tissue. The cartilage slices are digested at 37° C. for 1 hour with 0.4% Pronase (Calbiochem, La Jolla, Calif.) and then for 16 hours with 0.025% collagenase P from *Clostridium hystolyticum* (Boehringer Mannheim, Indianapolis, Ind.) in DMEM/F12 (Gibco BRL, Grand Island, N.Y.) containing 5% fetal bovine serum. The resulting digest is filtered through a 40-pm cell strainer (Cat #2340, Beckton Dickinson, Franklin Lakes, N.J.) and the chondrocytes are recovered. The chondrocytes are resuspended at a density of $4 \times 10^6$ cells/ml in a 1.2% solution of sterile alginate (Kelton LV, Kelco, Chicago, Ill.) in 0.15 M NaCl. The cell suspension is slowly expressed through a 22-gauge needle and dropped into a 102 mM calcium chloride solution. The beads are allowed to polymerize in this solution for 10 minutes and then washed twice in 0.15 M NaCl and then twice in DMEM/F12. The beads then are transferred to complete culture medium (200 beads in 10 ml) consisting of DMEM/F12, 10 µg/ml gentamicin, 20% fetal bovine serum, an effective amount of growth factor and 25 µg/ml ascorbic acid (Gibco BRL). The cultures are kept at 37° C. in a humidified atmosphere of 5% $CO_2$ in air with the medium replaced by fresh medium daily.

After 7 days of culture, the medium is collected and the beads dissolved at 4° C. by incubation for 20 minutes in 55 mM sodium citrate, 0.15 M NaCl, pH 6.8. The resulting suspension of cells (with their associated matrix) is centrifuged at 4° C. at 100 g for 10 minutes. The pellet, containing the cells with their cell-associated matrix, then is resuspended in DMEM/F12 containing 20% fetal bovine serum, an effective amount of growth factor and the supplements described above.

Three milliliters of complete medium are added to each well of a Falcon Cell Culture Insert Companion plate (Cat. #3090) and kept in the incubator at 37° C. in the presence of 5% $CO_2$ for 20 minutes. A Falcon Cell Culture Insert (Cat. #3090, 0.45 µm, PET membrane, transparent, diameter 23.1 mm, Beckton Dickinson) is aseptically placed into each well of a 6-well multiwell plate. A 2.5 ml aliquot (corresponding to the cells and their associated matrix present in 200 beads) is plated onto each Insert. The cultures are maintained at 37° C. in a humidified atmosphere of 5% $CO_2$. After 7 additional days in culture (referred to as days 8–14 of culture), each Insert is removed from the tissue culture plate and the PET membrane is cut using a scalpel. C haracterization of the Chondrocytes and Cartilage Matrix Formed after 7 Days of Culture in Alginate Beads On day 7, both (i) whole beads and (ii) the cells recovered with their cell-associated matrix after solubilization of the beads were fixed, sectioned and. visualized by phase contrast microscopy, as previously described. The matrix in both matrix compartments (cell-associated matrix and further removed matrix) was characterized for contents of proteoglycan, hyaluronan, collagen, and collagen crosslinks as described below.

Characterization of the Chondrocytes and Cartilage Matrix Formed After 7 Days of Culture in Alginate Beads Followed by 7 More Days of Culture on the Membrane On day 14, the morphological appearance of the tissue on the membrane was assessed by histology, its composition determined using a battery of biochemical assays, and the metabolism of the chondrocytes assessed in culture.

(i) Histology.

On day 14, the tissue, still on the PET membrane, was fixed using 4% paraformaldehyde in PBS and embedded in paraffin. Eight-µm-thick sections were cut and stained with Toluidine Blue for sulfated glycosaminoglycans. For electron microscopy, a small piece of tissue was cut and fixed in 2% glutaraldehyde, 0.1M sodium cacodylate buffer, 10 µM $CaCl_2$, pH 7.4.

(ii) Biochemical Composition of the Tissue.

At the end of the culture period (day 14), the tissue was removed from the membrane, blotted onto dry gauze and the wet weight measured. The tissue then was lyophilized and weighed again to obtain a measure of water content. The lyophilized tissue was digested at 56° C. for 24 hours with papain (20 µg/ml) in 0.1 M Sodium acetate, 50 mM EDTA, 5 mM cysteine hydrochloride, pH 5.53.

DNA content was measured using the bisbenzimidazole fluorescent dye [Hoechst 33258 (Polyscience, Warrington, Pa.)] method with calf thymus DNA as a standard.

Total content of sulfated glycosaminoglycan was determined by the dimethylmethylene blue (DMMB: Polyscience) assay as previously described.

Hydroxyproline content was measured by reverse-phase HPLC, using the PICO tag labeling technique, after hydrolysis of the sample for 16 hours at 110° C. in 6N HCl. Collagen content in each sample was estimated by multiplying the hydroxyproline content by 8.2.

Hyaluronan content was measured using sandwich ELISA technique as previously described and reported relative to the collagen content.

(iii) Characterization of Collagen Types Synthesized on Day 14of Culture.

On day 14 of culture (i.e. 7 days after the chondrocytes and their cell-associated matrix were placed upon the membrane of the tissue culture insert), the tissue on the membrane was incubated for 16 hours in DMEM containing [$^3$H]-proline at 50 µCi/ml, fetal bovine serum at 200 µl/ml, ascorbic acid at 25 µg/ml) and beta-aminoproprionitrile (BAPN) at 10 µg/ml to prevent crosslink formation. The tissue then was minced and extracted overnight with 1.0 M NaCl, 50 mM Tris containing proteinase inhibitors (1 mM N-ethylmaleimide, 1 mM phenylmethylsulfonyl fluoride, 5 mM EDTA) at 4° C. The residue was separated from the NaCl extract by centrifugation at 3000 rpm for 15 minutes and solubilized in 1% SDS. The labeling medium, the NaCl extract and the SDS fraction were dialyzed against distilled water to remove unincorporated isotopes. The samples were further dialyzed against 0.5M acetic acid and incubated overnight at 4° C. with pepsin (100µg/ml) in 0.2 M NaCl, 0.5 M acetic acid. The pepsin then was inactivated by the addition of NaOH in each sample to raise the pH to 8.6. The samples were further dialyzed against 0.4 M NaCl, 10 mM Tris, pH 7.4. Aliquots of the samples were analyzed by SDS-PAGE in an 8% acrylamide gel under reducing conditions. The gel was subjected to fluorography and the images were scanned and quantified as previously described.

(iv) Characterization of Proteoglycans Synthesized on Day 14of Culture.

On day 14of culture, the tissue was incubated for 4 hours in DMEM/F12 containing $^{35}$S-sulfate at 20 µCi/ml, 20% fetal bovine serum (200 µl/ml) and an effective amount of growth factor. The tissue then was extracted with 4 M guanidine chloride, 0.05 M sodium acetate, pH 6.0, in the presence of protease inhibitors as previously described. Radiolabeled proteoglycans were purified by DEAE column chromatography using a step-wise concentration gradient of sodium chloride. The purified proteoglycans were analyzed for size by sieve chromatography on Sepharose CL2B (Pharmacia) under dissociative conditions.

(v) Quantification of Collagen-Specific Crosslinks

Collagen-specific crosslinks (pyridinoline and deoxypyridinoline) were quantified using fluorescence detection following reverse-phase HPLC as previously described. Briefly, the samples were hydrolyzed in 6N HCl for 24 hours at 110° C. and the hydrolysates were applied to a CF-1 cellulose column to separate the crosslinking amino acids. The bound fraction was eluted with distilled water and dried. The samples were separated by reverse-phase HPLC on a C18 ODS column (Beckman) and the fluorescence of the eluted peaks was monitored using a spectrofluorimeter as previously described. The concentrations of crosslinking amino acid were reported as equivalents of external standards of pyridinoline and deoxypyridinoline.

vi) Measurement of Mechanical Property of the Cartilage Tissue Formed in vitro

The compressive and tensile properties of the transplantable construct were determined using standard methods. For compressive tests, disks (6.4 mm diameter) were cut from constructs and tested in a uniaxial confined compression apparatus on a mechanical testing machine (Dynastat: IMASS, Cambridge, Mass., USA) under computer control as described previously (15). Equilibrium load-dis placement data were acquired, and the equilibrium confined compression modulus was calculated using the formulation of Kwan et al (16). For tensile tests, tapered specimens (1 mm width in the gage region) were cut from constructs (17) and subjected to elongation at a constant strain rate until failure. The load at failure was normalized to the initial cross-sectional area to determine the ultimate stress. In all tests, samples were immersed in a physiological saline buffer.

RESULTS

Studies of the Matrix Formed after Seven Days of Culture in Alginate Beads

On day 7 of culture, tissue formed by chondrocytes cultured in the presence of growth factor contained an abundant, voluminous ECM. Examination of the cells in the beads by phase contrast microscopy showed evidence of only a moderate degree of cell division. After dissolving the beads with 55 mM sodium citrate in 0.9% NaCl, the cells and their associated matrix also were visualized.

The structure of this cell-associated matrix was well-preserved, consistent with the view that the cell-associated matrix is tightly bound to the cell membrane via cell-surface receptors such as CD44, integrins and anchorin CII. Biochemical analyses showed that the accumulated matrix was primarily composed of proteoglycan and to a lesser extent hyaluronan. It contained relatively little collagen immediately prior to transfer upon the membrane of the culture insert. Collagen-specific crosslinking was barely detectable at this stage.

Studies of the Matrix Formed after Seven Additional Days of Culture on the Membrane.

Between days 8 and 14 of culture, the individual cells and their associated matrix progressively became incorporated into a single mass of cartilagineous tissue.

Figure 4:
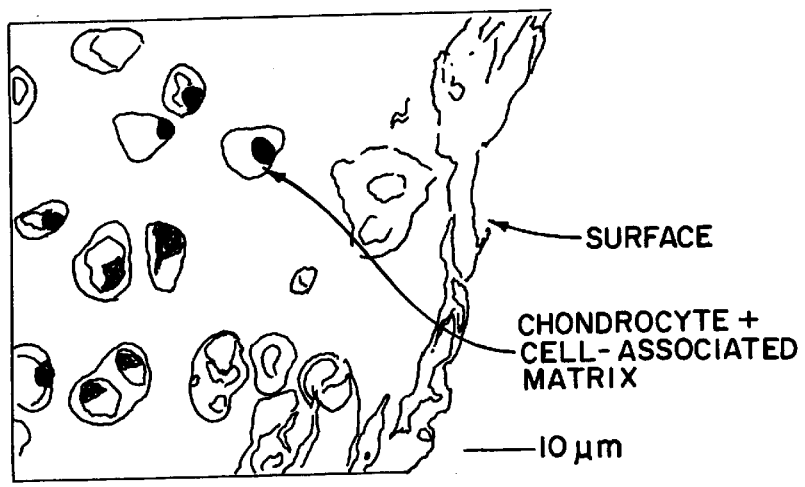
FIG. 4 shows the histological appearance of in vitro regenerated cartilage matrix produced in accordance with the present invention. Bovine articular chondrocytes were cultured with DMEM/F12 containing 20% FBS, an effective amount of growth factor, 10 µg/ml gentamicin and 25 µg/ml ascorbic acid in 1.2% alginate. After 7 days of culture, the beads were dissolved with 55 mM sodium citrate, 0.15 M sodium choloride, pH 6.8. The resulting suspension of the cell with their associated matrix is centrifuged at 100 g for 10 minutes. The pellet was resuspended in the same medium described above. After 7 additional days in culture, each insert was removed from the tissue culture plate and the tissue was processed for histology by Toluidine Blue Staining.

The regenerated cartilagineous tissue had a disk-like structure with a thickness of approximately one millimeter. The regenerated cartilage was readily recovered from the tissue culture insert by cutting the membrane. Histological examination of the tissue revealed it contained a cartilage-like matrix-that strongly stained with Toluidine blue and thus was rich in proteoglycans (FIG. 4). The staining was especially strong in the territorial (pericellular) areas of the matrix. Most of the chondrocytes were spherical in shape (as expected from chondrocytes that are phenotypically stable). A thin layer of flattened cells (similar in shape to the chondrocytes found in the most superficial layer of articular cartilage) were observed on the surface of the culture and on the interface to the membrane of the tissue culture insert. Examination in the electron microscope showed the presence of thin fibrils in the territorial areas and the absence of fibrils in the interterritorial area.

Biochemical analyses of the tissue on day 14of culture revealed that, as native articular cartilage matrix, it was very rich in proteoglycan and contained significant amounts of hyaluronan. In contrast, collagen was present at a much lower concentration than in cartilage. Further, the concentration of pyridinoline crosslinks (18 mmol/mnol collagen), which by crosslinking the collagen fibrils make the fibrillar network more difficult to resorb, was very much lower than in articular cartilage. Although the stiffness of this tissue was considerably lower than that of normal adult articular cartilage, the tissue nevertheless was easy to handle. It should be easy for to orthopedic surgeons to press-fit it, if needed, into a defect in the articular cartilage surface. Preferably, this cartilaginous tissue should be dissected into a size that is 0.5 mm larger. than the real defect to allow the surgeon to press-fit it into the defect: such a fit would allow the implanted tissue to make close contact with the patient's cartilage. This approach may prove useful in maximizing its integration within the articular tissue of the patient.

Aggrecan, the major proteoglycan of normal articular, cartilage, made up more than 90% of the $^{35}$S-proteoglycans synthesized on day 14 of culture and incorporated into the matrix. Small nonaggregating $^{35}$S-proteoglycans were recovered from the tissue in much smaller amounts. nalysis of the newly synthesized collagens showed that the chondrocytes produced mostly the cartilage-specific collagen type II, although small amounts of other artilage collagens were detected.

Measurement of Mechanical Property of the Cartilage Tissue Formed in vitro revealed that the equilibrium confined compression modulus after 1 week of culture in the insert was 0.001 MPa, which is markedly lower than normal full thickness cartilage (about 0.4 MPa). At the same time point, the peak tensile stress was 0.01 Mpa, which was also lower than normal full cartilage. However, both values increased markedly with time in culture.

Example II

In Vivo Animal Study

Preparation of the Tissue to be Implanted. The articular cartilage from rabbits weighing 1–1.5 kg was dissected from each joint and digested with pronase and collagenase sequentially. The chondrocytes thus obtained were encapsulated in alginate beads and cultured for 1 week. After 12 weeks, the beads were dissolved by addition of sodium citrate solution and the cells with their cell-associated matrix recovered by mild centrifugation. After washing with physiological saline, the cells were placed into a tissue culture insert (Falcon, CAT #3090) and allowed to reform a cartilage-like tissue over seven days of culture in DMEM/Ham F-12 medium supplemented with 20% FBS, 25 µg/ml ascorbic acid, 10µg/ml gentamicin. The grafts for transplantation were then removed from the tissue culture insert and placed into sterile culture tubes.

Transplantation. Twelve male rabbits (3–3.5 kg) underwent surgery. After general anesthesia with ketamine and xylozine followed by isoflurane inhalation, the rabbit was placed in a supine position. Following proper sterilization and draping, the knee joints were exposed through a medial parapatellar approach. An incision of the capsule was performed and the patella was dislocated laterally. A 3.5 mm-full thickness cartilage defect was made (using a biopsy punch) at the center of the patellar groove. The defects was then treated as follows. Group 1 (control): the defect was not treated. Group 2 (cartilaginous graft): a cartilaginous graft (generated as described above) was placed into the defect In all cases, the joint was then washed several times with sterile saline containing antibiotics and closed with layered sutures. The animal was allowed to recover from anesthesia in the cage. After 4 weeks, the animals were euthanatized as described above and a photograph of cartilage surface was taken.

Figure 5:
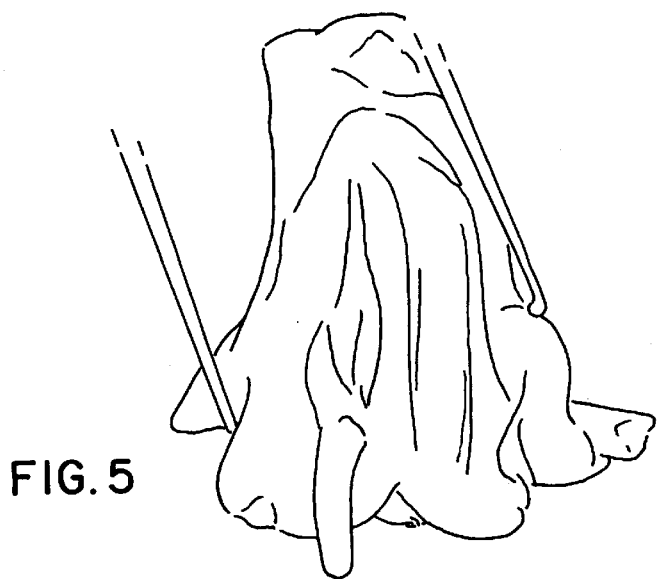
FIG. 5 shows repair of a cartilage defect one month after reimplantation of the cartilage tissue formed in vitro.

Results:

The defect in Group 1 showed partial spontaneous repair by a white scar tissue. On the other hand, the defect in Group 2 was filled with transparent cartilage whose surface resembled the surface of normal articular cartilage (FIG. 5).

Numerous modifications and variations in the practice of the invention are expected to occur to those skilled in the art upon consideration of the foregoing detailed description of the invention. Consequently, such modifications and variations are intended to be included within the scope of the following claims.

REFERENCES

1. A. I. Caplan, *Nippon Seikeigeka Gakkai Zasshi* 63, 692–9 (1989).
2. R. G. Johnson, A. R. Poole, *Exp.Pathol.* 38, 37–52 (1990).
3. R. Mayne, in *Structure and Function of Articular Cartilage* V. C. Mow, A. Ratcliffe, Eds. (CRC Press, Inc., Boca Raton, 1993) pp. 1–48.
4. J. A. Buckwalter, J. C. Pita, F. J. Muller, J. Nessler, *Journal of Orthopaedic Research* 12, 144–148 (1994).
5. J. R. Harper, *ECM.Connections*. 1, 1–4 (1990).
6. L. A. MacGinitie, Y. A. Gluzband, A. J. Grodzinsky, *J Orthop Res* 12, 151–60 (1994).
7. J. Mizrahi, A. Maroudas, Y. Lanir, I. Ziv, T. J. Webber, *Biorheology*. 23, 311–330 (1986).
8. C. B. Knudson, *J.Cell Biol.* 120, 825–834 (1993).
9. J. J. Wu, P. E. Woods, D. R. Eyre, *J. Biol. Chem.* 267, 23007–23014 (1992).
10. D. A. Hendrickson, et al., *J Orthop Res* 12, 485–97 (1994).
11. H. J. Hauselmann, et al., *Am J Physiol* 271, C742–52 (1996).
12. D. A. Grande, M. I. Pitman, L. Petersen, D. Menche, M. Klein, *Journal of Orthopaedic Research* 7, 208–218 (1989).
13. M. P. Fernandez, et al., *J.Biol.Chem.* 263, 5921–5925 (1988).
14. K. Von Der Mark, *Rheumatology* 10, 272–315 (1986).
15. R. M.Schinagl, et al., *J Orthop Res*. 15: 499–506, (1997).
16. M. K. Kwan, et al., *J Biomech Eng*. 114: 149–153, (1992).
17. G. E. Kempson, *Biochem Biophys Acta*. 1075: 223–230, (1991).

What is claimed is:

1. A method for the production of transplantable cartilage matrix, the method comprising:
    isolating chondrogenic cells;
    culturing chondrogenic cells in an alginate medium for an amount of time effective for allowing formation of a chondrogenic cell-associated matrix;
    recovering the chondrogenic cells with the cell-associated matrix; and
    culturing the chondrogenic cells with the cell-associated matrix on a semipermeable membrane in the presence of growth factor for a time effective for allowing formation of a cartilage matrix.

2. A method for the production of transplantable cartilage matrix according to claim 1 wherein the chondrogenic cell-associated matrix includes aggrecan, collagen types II, IX and XI, and hyaluronan.

3. A method for the production of transplantable cartilage matrix according to claim 2 wherein the ratio aggregan to hyaluronan in the chondrogenic cell-associated matrix is at least above about 10:1.

4. A method for the production of transplantable cartilage matrix according to claim 1 wherein the semipermeable membrane has a pore size of less than about 5 microns and a pore density of at least about $8 \times 10^5$ pores per $cm^2$.

5. A method for the production of transplantable cartilage matrix according to claim 1 wherein the growth factor is selected from the group consisting of osteogenic protein-1, bone morphogenetic proteins, transforming growth factor beta, insulin-like growth factor, and mixtures thereof.

6. A method for the production of transplantable cartilage matrix according to claim 1 wherein the cartilage matrix includes aggrecan, collagen types II, IX and XI, and hyaluronan.

7. A method for the production of transplantable cartilage matrix according to claim 6 wherein the cartilage matrix has a ratio aggregan to hyaluronan of at least above about 10:1.

8. A cohesive cartilage matrix produced by a method comprising:
    isolating chondrogenic cells;
    culturing chondrogenic cells in an alginate medium for an amount of time effective for allowing formation of a chondrogenic cell-associated matrix;
    recovering the chondrogenic cells with the cell-associated matrix; and
    culturing the chondrogenic cells with the cell-associated matrix on a semipermeable membrane in the presence of growth factor for a time effective for allowing formation of a cohesive cartilage matrix.

9. A cohesive cartilage matrix according to claim 8 wherein the chondrogenic cell-associated matrix includes aggrecan, collagen types II, IX and XI, and hyaluronan.

10. A cohesive cartilage matrix according to claim 9 wherein the ratio aggregan to hyaluronan in the chondrogenic cell-associated matrix is at least above about 10:1.

11. A cohesive cartilage matrix according to claim 8 wherein the semipermeable membrane has a pore size of less than about 5 microns and a pore density of at least about $8 \times 10^5$ pores per cm$^2$.

12. A cohesive cartilage matrix according to claim 8 wherein the growth factor is selected from the group consisting of osteogenic protein-1, bone morphogenetic proteins, transforming growth factor beta, insulin-like growth factor, and mixtures thereof.

13. A cohesive cartilage matrix according to claim 8 wherein the cohesive cartilage matrix includes aggrecan, collagen types II, IX and XI, and hyaluronan.

14. A cohesive cartilage matrix according to claim 13 wherein the cohesive cartilage matrix has a ratio aggregan to hyaluronan of at least above about 10:1.

15. A method for the surgical repair of cartilage damage comprising:

producing a transplantable cartilage matrix, wherein the transplantable cartilage matrix is produced by a method comprising isolating chondrogenic cells; culturing chondrogenic cells in an alginate medium for an amount of time effective for allowing formation of a chondrogenic cell-associated matrix; recovering the chondrogenic cells with the cell-associated matrix; and culturing the chondrogenic cells with the cell-associated matrix on a semipermeable membrane in the presence of growth factor for a time effective for allowing formation of a cartilage matrix; and surgically implanting the cartilage matrix.

16. A method for the surgical repair of cartilage damage according to claim 15 wherein the chondrogenic cell-associated matrix includes aggrecan, collagen types II, IX and XI, and hyaluronan.

17. A method for the surgical repair of cartilage damage according to claim 16 wherein the ratio aggregan to hyaluronan in the chondrogenic cell-associated matrix is at least above about 10:1.

18. A method for the surgical repair of cartilage damage according to claim 15 wherein wherein the semipermeable membrane has a pore size of less than about 5 microns and a pore density of at least about $8 \times 10^5$ pores per cm$^2$.

19. A method for the surgical repair of cartilage damage according to claim 15 wherein wherein the growth factor is selected from the group consisting of osteogenic protein-1, bone morphogenetic proteins, transforming growth factor beta, insulin-like growth factor, and mixtures thereof.

20. A method for the surgical repair of cartilage damage according to claim 15 wherein the cartilage matrix includes aggrecan, collagen types II, IX and XI, and hyaluronan.

21. A method for the surgical repair of cartilage damage according to claim 20 wherein the cartilage matrix has a ratio aggrecan to hyaluronan of at least above about 10:1.

22. A cohesive cartilage matrix comprising:

at least about 5 mg/cc$^3$ aggrecan;

collagen types II, IX and XI, and hyaluronan, wherein the ratio of aggrecan to hyaluronan is about 10:1 to about 200:1, and the ratio of aggrecan to collagen is about 1:1 to about 10:1.

23. A cohesive cartilage matrix according to claim 22 wherein the matrix has a thickness of less than about 2 mm.

\* \* \* \* \*